(12) United States Patent
Peszynski et al.

(10) Patent No.: US 9,339,253 B2
(45) Date of Patent: May 17, 2016

(54) ULTRASOUND PROBE HAVING A DISINFECTION STATUS INDICATOR

(75) Inventors: Michael Peszynski, Newburyport, MA (US); Heather Knowles, Devens, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 2485 days.

(21) Appl. No.: 11/912,514

(22) PCT Filed: Apr. 20, 2006

(86) PCT No.: PCT/IB2006/051224
§ 371 (c)(1),
(2), (4) Date: Oct. 25, 2007

(87) PCT Pub. No.: WO2006/114733
PCT Pub. Date: Nov. 2, 2006

(65) Prior Publication Data
US 2008/0188754 A1 Aug. 7, 2008

Related U.S. Application Data

(60) Provisional application No. 60/674,491, filed on Apr. 25, 2005.

(51) Int. Cl.
| | | |
|---|---|---|
| *A61B 8/08* | (2006.01) | |
| *A61B 8/00* | (2006.01) | |
| *A61B 19/00* | (2006.01) | |
| *A61N 7/00* | (2006.01) | |

(52) U.S. Cl.
CPC . *A61B 8/00* (2013.01); *A61B 8/467* (2013.01); *A61B 8/461* (2013.01); *A61B 2019/4873* (2013.01); *A61B 2560/0276* (2013.01); *A61N 7/00* (2013.01)

(58) Field of Classification Search
CPC .......... A61B 8/00; A61B 8/467; A61B 8/461; A61B 2560/0276; A61B 2019/4873; A61N 7/00
USPC .................. 600/459; 367/140, 153, 155, 157; 73/584, 596, 627–634
See application file for complete search history.

(56) References Cited

U.S. PATENT DOCUMENTS

| | | |
|---|---|---|
| 5,359,993 A | 11/1994 | Slater |
| 5,782,769 A | 7/1998 | Hwang |

(Continued)

FOREIGN PATENT DOCUMENTS

| | | |
|---|---|---|
| JP | 7391 | 1/1995 |
| JP | 1156838 | 3/1999 |

(Continued)

*Primary Examiner* — Jonathan Cwern

(57) ABSTRACT

An ultrasound probe (202) having an operational indicator assembly (204) for indicating operational data relating to the ultrasound probe (202), and especially data relating to the sterility of the ultrasound probe (202), is provided. The ultrasound probe (202) has a housing (203) fabricated from materials suitable for internal and non-internal medical use. At least one ultrasound transducer (209) is housed by the housing (203) and positioned to direct ultrasound energy along a propagation path to the patient. The operational indicator assembly (204) indicates operational data relating to the ultrasound probe (202) to an operator thereof, and especially data relating to the disinfection status of the ultrasound probe (202).

15 Claims, 3 Drawing Sheets

(56) References Cited

U.S. PATENT DOCUMENTS

| | | |
|---|---|---|
| 5,817,024 A | 10/1998 | Ogle et al. |
| 6,139,496 A | 10/2000 | Chen |
| 6,270,460 B1 | 8/2001 | McCartan |
| 6,387,092 B1 | 5/2002 | Burnside |
| 2004/0002657 A1 | 1/2004 | Marian |
| 2005/0014214 A1 | 1/2005 | Eveland |
| 2005/0021019 A1 | 1/2005 | Hashimshony |
| 2005/0131301 A1* | 6/2005 | Peszynski et al. ............ 600/459 |
| 2006/0155914 A1* | 7/2006 | Jobs et al. .................... 711/100 |

FOREIGN PATENT DOCUMENTS

| | | |
|---|---|---|
| JP | 2001166222 | 6/2001 |
| JP | 2003274646 | 9/2003 |
| WO | 03079888 A2 | 10/2003 |
| WO | 2004107980 | 12/2004 |

* cited by examiner

ULTRASOUND PROBE HAVING A DISINFECTION STATUS INDICATOR

BACKGROUND OF THE DISCLOSURE

1. Field of the Invention

The present disclosure relates generally to ultrasound probes used in medical diagnostic and treatment procedures. In particular, the present disclosure relates to an ultrasound probe having an operational indicator assembly.

2. Description of the Related Art

Medical ultrasound imaging has become a popular means for visualizing and medically diagnosing the condition and health of interior regions of the human body. With this technique, a disinfected ultrasound probe having an array of acoustic transducers or a single transducer, in operative communication with an ultrasound system console via an interconnection cable, is provided against the patient's tissue or inserted within the patient's gastrointestinal tract where it is actuated to emit and receive focused ultrasound waves in a scanning fashion. The scanned ultrasound waves, or ultrasound beams, allow the systematic creation of image slices of the patient's internal tissues for display on a monitor of the ultrasound system console.

During ultrasonic imaging, the disinfected ultrasound probe is susceptible to becoming contaminated. Accordingly, it is an object of the present disclosure to present a system for providing operational data relating to the ultrasound probe, and especially data relating to the disinfection state of the ultrasound probe.

SUMMARY OF THE DISCLOSURE

The present disclosure provides an ultrasound probe having an operational indicator assembly for indicating operational data relating to the ultrasound probe, and especially data relating to the disinfection state of the ultrasound probe. In particular, the present disclosure provides an ultrasound probe having a housing fabricated from materials suitable for internal and non-internal medical use. At least one ultrasound transducer is housed by the housing and positioned to direct ultrasound energy along a propagation path to the patient. The operational indicator assembly indicates operational data relating to the ultrasound probe to an operator thereof, and especially data relating to the disinfection state of the ultrasound probe.

In particular, the present disclosure provides an ultrasound probe having a housing; at least one ultrasound transducer within the housing and positioned to direct ultrasound energy along a propagation path; and an operational indicator assembly provided to the housing and having means for controlling at least one indicator system for indicating at least one operational characteristic relating to the ultrasound probe. The at least one indicator system can include a plurality of LEDs or a liquid crystal display (LCD) for indicating the at least one operational characteristic relating to the ultrasound probe. One of the at least one operational characteristic indicated by the at least one indicator system relates to the disinfection status of the ultrasound probe.

Preferably, the means for controlling includes a programming button positioned on the housing for transmitting at least one signal to at least one processor and/or EEPROM for controlling the at least one indicator system.

BRIEF DESCRIPTION OF THE DRAWINGS

These and other features, aspects, and advantages of the present disclosure will become better understood with regard to the following description, appended claims, and accompanying drawings wherein:

DESCRIPTION OF THE PREFERRED EMBODIMENTS

Figure 1:
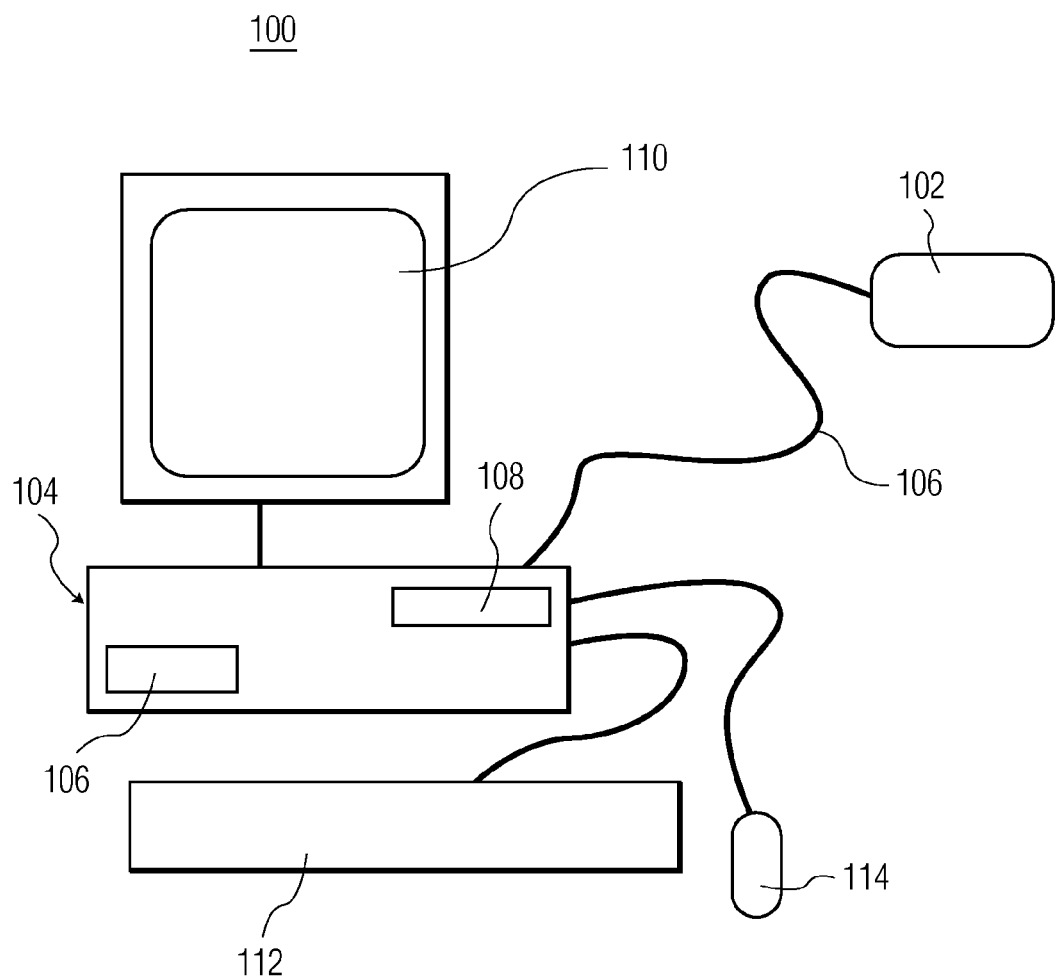
FIG. 1 is an illustration of a prior art ultrasound medical imaging system.

Referring to FIG. 1 a prior art medical ultrasound imaging system 100 is shown. The system 100 includes an ultrasound imaging probe 102 connected to an imaging workstation 104. The imaging workstation 104 contains one or more processors 106 and at least one storage device 108, such as a hard drive, RAM disk, etc. The storage device(s) 108 may be used for storing the controlling and imaging software for the ultrasound system 100 as well as providing temporary and long term storage of image data acquired by the ultrasound probe 102. The ultrasound imaging system 100 also provides a video display 110 and user input devices, including a keyboard 112 and a mouse 114.

The processor 106 is configured to execute controlling and imaging software. The imaging software allows the operator of the system 100 to visualize and manipulate the data received from the ultrasound probe 102.

Figure 2:
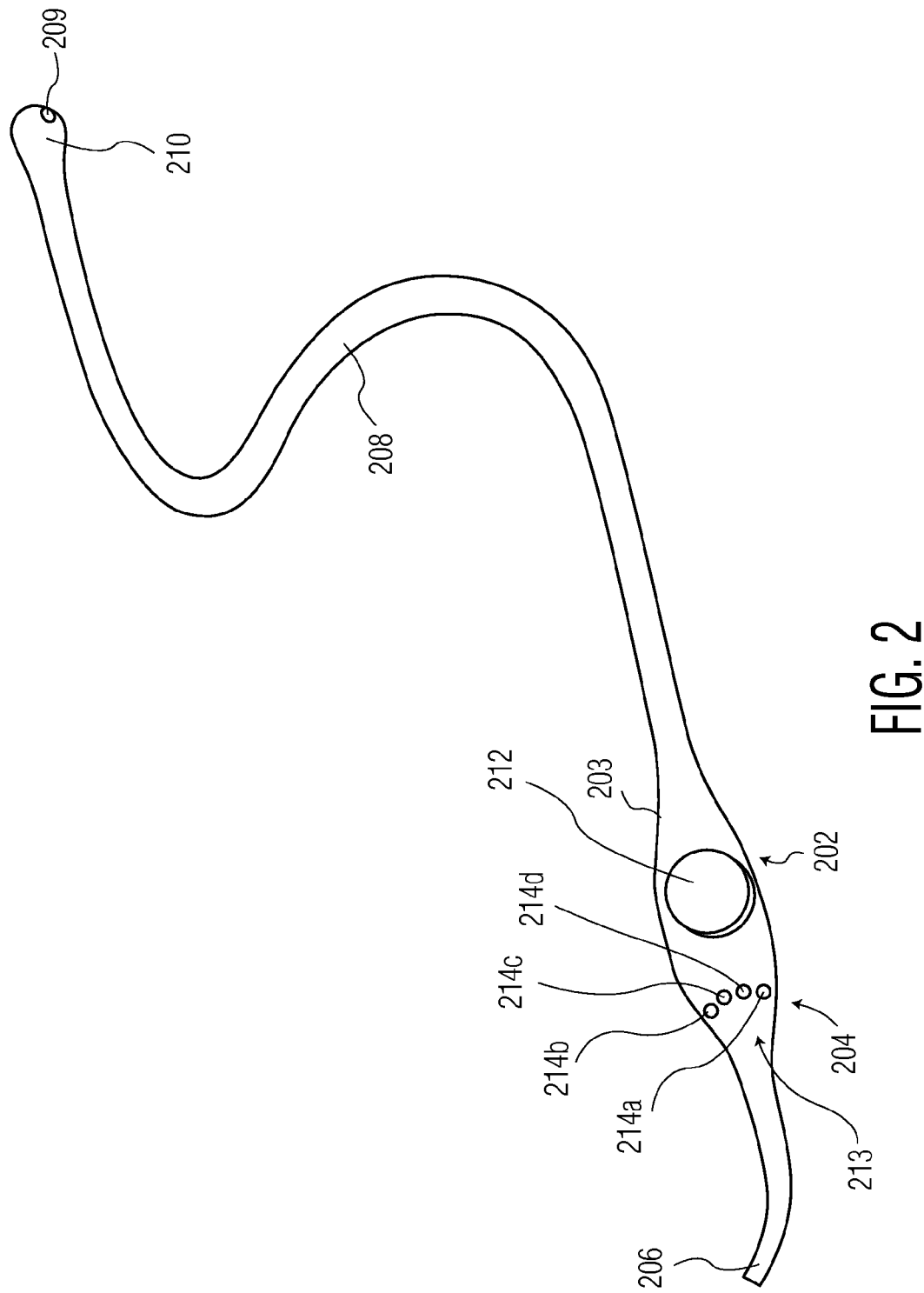
FIG. 2 illustrates an exemplary embodiment of an ultrasound probe having an operational indicator assembly and configured for internal use in accordance with the present disclosure.
Figure 3:
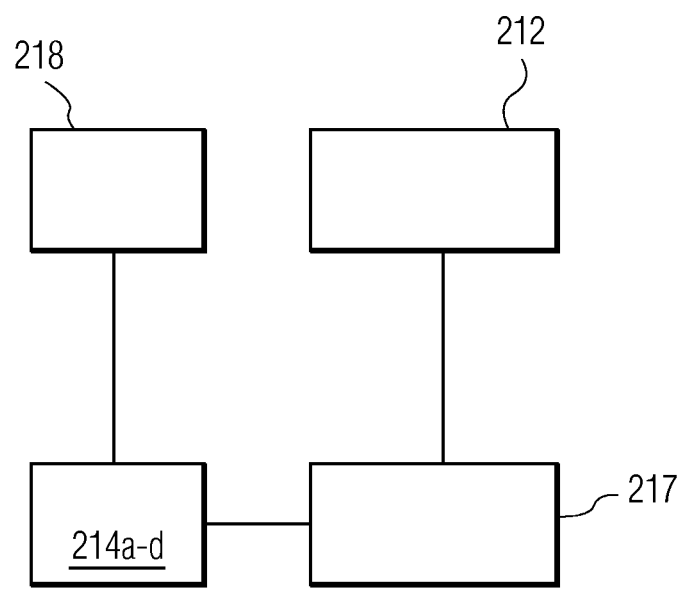
FIG. 3 illustrates a block diagram of the ultrasound probe shown by FIG. 2.

An exemplary embodiment of the present disclosure, as shown in FIG. 2, provides an ultrasound medical imaging probe 202 having a housing 203 and an operational indicator assembly 204 for indicating operational data relating to the ultrasound probe 202 to an operator thereof, and especially data relating to the disinfection status of the ultrasound probe 202. The probe 202 further includes a cable 206 for connecting to an imaging workstation, such as imaging workstation 104 shown by FIG. 1. An articulating stalk 208 is provided for enabling the probe 202 to be inserted into a patient's gastrointestinal tract for performing imaging operations as known in the art. A distal end 210 of the articulating stalk 208 houses an ultrasound transducer array or an ultrasound transducer 209 and related imaging circuitry as known in the art for performing the imaging operations.

In one embodiment, the operational indicator assembly 204 includes a programming button 212 and an indicator system 213 having a series of LEDs 214a-d positioned in proximity to the programming button 212 for indicating operational information to an operator of the probe 202, including information relating to the disinfection status of the probe 202. In accordance to which LEDs 214a-d are lit, the operator associates the lit LEDs as forming a code which is then used to determine information regarding the probe 202. The information is determined by corresponding the code to at least one rule of a set of predetermined rules. For example, if none of the LEDs 214a-d are lit, then the probe 202 is high level disinfected (e.g., code: none lit; rule: probe is high level disinfected). If LED 214a is lit, then the probe 202 has been sterilized.

Other operational data can also be indicated by lighting one or more of the LEDs 214a-d, such as visual inspection has passed, electrical test status, and the probe 202 needs to be serviced. Correspondingly, the LEDs could indicate this status. For example, if LED 214b is lit, the probe has passed visual inspection. If LED 214 c is lit, the probe has passed an electrical safety test, etc. The LEDs 214a-d are progressively lit by the operator pressing on programming button 212 to indicate the disinfection status of the probe and other data. For example, if none of the LEDs 214a-d are lit and the operator presses the programming button 212 one time, LED 214a is lit; two times, LED 214b is lit; three times, LED 214c is lit; four times, LED 214d is lit; five times, LEDs 214a and 214b are lit; six times, LEDs 214a and 214c are lit; seven times, LEDs 214a and 214d are lit; eight times, LEDs 214b and 214c are lit; and so on.

Other configurations are envisioned within the scope of the present disclosure for indicating operational data relating to the probe 202, including data relating to the disinfection status of the probe 202, using the LEDs 214a-d of the operational indicator assembly 204. For example, LED 214a can be a green LED which is lit automatically or manually when the probe 202 is actuated for performing an imaging operation, and LED 214b can be a red LED which is lit automatically or manually when the probe 202 is de-actuated following the imaging operation to indicate the probe 202 is no longer disinfected or sterile.

By pressing the programming button 212, at least one processor and/or EEPROM 217 within the probe 202 is programmed to light the one or more LEDs 214a-d as described above for indicating operational data relating to the probe 202. It is also envisioned for the indicator assembly 213 to include a liquid crystal display (LCD) or other indicator means for indicating and/or displaying operational data, including data relating to the disinfection status of the probe 202.

The LEDs 214a-d provide a quick and efficient safety check regarding the operational and disinfection status of the probe 202, prior to the use of the probe 202 by the operator. The LEDs 214a-d are powered by the imaging system 100 when the probe 202 is plugged thereto and by a battery 218 housed by the probe 202 when the probe 202 is unplugged from the imaging system 100. The battery 218 is preferably a rechargeable nickel metal hydride battery as known in the art.

In another embodiment, the disinfection status of the probe 202 can be programmed electronically by operatively interfacing the probe 202 to an automated disinfection machine (automated reprocessor), which programs the at least one processor and/or EEPROM 217 and changes the status indicator LEDs 214a-d, based on the probe 202 passing or failing the disinfection cycle, as specified in the reprocessor software. Similarly, the probe 202 could be operatively interfaced with a leakage current tester, which programs the at least one processor and/or EEPROM 217 to allow display of the status on the probe 202 and on a display of the leakage current tester. Additionally, in either of these embodiments, the at least one processor and/or EEPROM 217 could lock out usage of the probe 202 under unsafe conditions.

The imaging workstation 104 can be used to interrogate at least one processor and/or EEPROM 217 for receiving signals relating to operational data of the probe 202. The imaging workstation 104 can then interpret the signals and display the operational data on the video display 110 for viewing by the operator and printing by a printer.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

The invention claimed is:

1. An ultrasound probe comprising:
   a housing;
   at least one ultrasound transducer within the housing and positioned to direct ultrasound energy along a propagation path; and
   an operational indicator assembly provided to the housing and having at least one indicator system for indicating the disinfection status of said ultrasound probe, wherein the indicator system indicates (i) that the probe has been sterilized and, if not, then (ii) that the probe is no longer disinfected or sterile.

2. The ultrasound probe according to claim 1, wherein said at least one indicator system includes a plurality of LEDs.

3. The ultrasound probe according to claim 1, wherein said at least one indicator system includes a liquid crystal display (LCD).

4. The ultrasound probe according to claim 2, wherein said indicator system further comprises a first LED which, when lit, indicates that the probe has been sterilized, and a second LED which, when lit, indicates that the probe is no longer disinfected or sterile, wherein the LEDs indicate the disinfection status of the ultrasound probe.

5. The ultrasound probe according to claim 1, wherein the operational indicator assembly further comprises a programming button positioned on the housing for transmitting at least one signal to at least one processor for controlling the at least one indicator system.

6. The ultrasound probe according to claim 5, wherein the at least one processor further comprises an EEPROM for controlling the at least one indicator system.

7. The ultrasound probe according to claim 1, wherein the operational indicator assembly is further operable to prevent operation of the probe based on the disinfection status relating to said probe.

8. The ultrasound probe according to claim 1, further comprising means for operatively connecting said probe to an imaging workstation capable of controlling the at least one indicator system.

9. A method for indicating the disinfection status of an ultrasound probe, the method comprising:
   providing an operational indicator assembly to the probe having an indicator system for indicating the disinfection status relating to said probe; and
   activating the operational indicator assembly to display a code via the indicator system, wherein said code corresponds to the disinfection status in accordance with a set of predetermined rules which produce a visual indication that (i) the probe has been sterilized and, if not, then (ii) that the probe is no longer disinfected or sterile.

10. The method according to claim 9, wherein said provided indicator system includes a plurality of LEDs.

11. The method according to claim 9, wherein said provided indicator system includes a liquid crystal display.

12. The method according to claim 9, wherein the provided operational indicator assembly further comprises a programming button for transmitting at least one signal to at least one processor for controlling the at least one indicator system.

13. The method according to claim 12, wherein the at least one processor further comprises an EEPROM for controlling the at least one indicator system.

14. The method according to claim 9, wherein provided operational indicator assembly is further operable to prevent operation of the probe based on the disinfection status relating to said probe.

15. The method according to claim 9, further comprising operatively connecting said probe to an imaging workstation capable of controlling the indicator system.

* * * * *